United States Patent [19]

Chang et al.

[11] Patent Number: 4,792,683

[45] Date of Patent: Dec. 20, 1988

[54] THERMAL TECHNIQUE FOR SIMULTANEOUS TESTING OF CIRCUIT BOARD SOLDER JOINTS

[75] Inventors: David B. Chang, Tustin; Michael F. Berg, Fruita; James E. Drummond, Oceanside; Lee Mickelson, Long Beach, all of Calif.

[73] Assignee: Hughes Aircraft Company, Los Angeles, Calif.

[21] Appl. No.: 4,009

[22] Filed: Jan. 16, 1987

[51] Int. Cl.[4] .................... G01N 21/71; G01N 25/72
[52] U.S. Cl. ................................. 250/341; 250/334
[58] Field of Search .......... 250/341, 340, 334, 338 R; 374/5, 57

[56] References Cited

U.S. PATENT DOCUMENTS

| | | | |
|---|---|---|---|
| 3,808,439 | 4/1974 | Renius | 250/334 |
| 4,240,750 | 12/1980 | Kurtz et al. | 356/394 |
| 4,481,418 | 11/1984 | Vanzetti et al. | 250/338 |
| 4,647,220 | 3/1987 | Adams et al. | 374/5 |

FOREIGN PATENT DOCUMENTS 218938  12/1984  Japan .................. 250/341

396609  8/1973  U.S.S.R. ................ 374/5

OTHER PUBLICATIONS

R. W. Jones and L. M. White, "Infrared Evaluation of Multilayer Boards", Materials Evaluation, (Feb. 1969) pp. 37–41.

Primary Examiner—Janice A. Howell
Assistant Examiner—Constantine Hannaher
Attorney, Agent, or Firm—Leonard A. Alkov; A. W. Karambelas

[57] ABSTRACT

A system for inspecting the electronic integrity of solder joints by repetitive pulse-heating the solder joints with radiant energy and determining the temperature oscillation of pulse-heated solder joints by measuring the infrared emissions from the solder joints during heating and non-heating periods. Advantageously, the exposed solder joints of a circuit board can be tested all at one time by pulse-heating the entire circuit board. The temperature oscillation of each joint can be compared to the temperature oscillations of corresponding standard solder joints of known good electronic integrity on properly operating boards.

36 Claims, 6 Drawing Sheets

THERMAL TECHNIQUE FOR SIMULTANEOUS TESTING OF CIRCUIT BOARD SOLDER JOINTS

FIELD OF THE INVENTION

This invention relates to a non-destructive, non-contact apparatus and method for testing or inspecting the electronic integrity of solder joints on a circuit board employing thermal detection methods.

BACKGROUND OF THE INVENTION

Various methods have been developed for the qualitative inspection of the electronic integrity of a solder joint, including sonic and ultrasonic testing methods with or without an electric current load; thermal testing methods to determine the heating and cooling-off responses of a solder joint, and X-ray analysis of solder joints. These methods are slow, tedious, and have not received universal acceptance because of the lack of proven performance and of the testing equipment cost associated therewith.

Vanzetti (U.S. Pat. No. 4,481,418) has demonstrated that thermal information is useful for determining the electronic integrity of a solder joint. In the Vanzetti system, a laser beam sequentially illuminates and heats each solder joint on a circuit board individually. The energy imparted to a joint raises the joint's temperature, and an infrared sensor sequentially measures the rate at which the temperature rises and decays for each joint during the illumination thereof with the laser beam. In a bad joint (i.e., a joint in which the contact with the desired electrical conductors is poor) the initial temperature rises very high during illumination, then will decay more slowly than for a good joint following illumination. The Vanzetti technique has been shown in some cases to be a sensitive and reliable detector of deficient joints. However, the Vanzetti system requires that the laser heating source must be focused, and has to be mechanically moved from solder joint to solder joint to spot-heat each solder joint individually, with the attendant registration and programming problems. In addition, the Vanzetti system heats and reads each solder joint in a single pulse, and thus does not address a stabilized system. It does not permit repeated readings to improve the signal-to-noise ratio. Within an improved signal-to-noise ratio, smaller temperature swings can be measured to determine the electronic integrity of a particular joint. In addition, since the Vanzetti system relies on direct laser illumination of a joint to heat the joint, the technique is quite sensitive to surface contamination of the joint. This contamination can cause appreciable changes in the already low emissivity- and therefore absorption - of the joint to the laser radiation.

The present system overcomes many of the disadvantages of the existing systems because of its speed, reproducibility and flexibility in that existing testing equipment can quickly and inexpensively be modified to carry out the system of the present invention. The present system illuminates the entire board, which permits a more efficient coupling of heat into the solder joints via connecting conductors, and improves the signal-to-noise ratio because surface contamination effects are reduced. In addition, no focusing or mechanical motion of the heating source is required; a simple, fixed heating source can be used. Further, the present system uses repetitive heating pulses, permitting detection of oscillating joint temperature excursions, which permits the signal-to-noise ratio improvement.

SUMMARY OF THE INVENTION

The present invention is directed to a method for inspecting the electronic integrity of a solder joint comprising the steps of:

(a) applying repetitively pulsed radiant energy to a solder joint and exposed connecting conductors to heat the joint, causing it to radiate infrared radiation;

(b) measuring the time course of infrared emission from the solder joint; and (c) comparing the infrared radiation profile of a solder joint of known good electronic integrity with the infrared radiation profile of the solder joint undergoing inspection.

In the preferred embodiment of the invention, a plurality of solder joints on a circuit board are analyzed simultaneously by heating the side of the circuit board with the exposed solder joints by flood-heating, that is, heating the entire board at one time rather than spot-heating each joint. Preferably, the heating and reading cycles are pulsed at 10 Hz or less. The solder joints are preferably read, that is, measuring of the infrared emission from the joints, during the heating pulse and the time between heating pulses to determine the rate of heating and cooling and the amplitude of the temperature change. The solder joints are illuminated with a high-intensity ambient light source or with an infrared source to raise the temperature of the solder joints to an elevated temperature not exceeding 100° C. Preferably, the heating pulse is from between about 50 milliseconds and 500 milliseconds, and the period between pulses is between about 50 and about 950 milliseconds. The heating or work cycle is at least about 10%, preferably about 50%, so that the joint is heated and not heated for approximate equal periods. Alternatively, for boards with plated-through holes, the board can be illuminated and read on the side opposite the exposed solder joints.

In the present invention, all the solder joints on a circuit board are tested simultaneously. The entire board is radiated by repetitively pulsed radiant sources at a repetition of about 1 Hz to about 10 Hz. The periodic time course of the thermal image of the board is monitored with an infrared detector. The signal generated by the infrared detector is stored in a memory means, such as a small mini- or micro-computer. The amplitude of the periodic temperature variation of a solder joint (See FIG. 3) is determined by the goodness of the joint, as well as by the local environment of the joint, that is, the number and conductivity of connecting circuit traces. By comparing the amplitudes of the temperature oscillations (T-oscillations) of the solder joints on the board under test, with those stored in memory, of a substantially identical board having solder joints of known good electronic integrity, the local environmental effects around each solder joint are subtracted out, so that deficient joints can be identified. Deficient joints show different amplitude of temperature change and rate and shape of temperature change from good joints at repetition periods comparable to the time it takes the heat to diffuse between the solder joint and its connecting conductors.

In a more sophisticated version, the phases of the temperature oscillation can be compared and, in addition, a fast Fourier transform of the temperature time variation can be obtained and various moments of the transform compared.

The present method employs an apparatus for inspecting the electronic integrity of a solder joint comprising:

(a) a radiation source for flood-heating the solder joint and exposed connecting conductors and surrounding board substrate to cause the heated solder joint to radiate infrared radiation;

(b) an infrared detector for detecting infrared radiation emitted from said heated solder joint and for generating a signal proportional to the amplitude of the detected infrared radiation;

(c) means to convert the signals from the infrared detector into machine-readable inspection information;

(d) memory means for storing the machine-readable inspection information and machine-readable standard information depicting an infrared profile of a substantially identical solder joint of known good electronic integrity; and (e) means to compare the machine-readable inspection information against the machine-readable standard information so as to identify deviate solder joints of substandard electronic integrity.

In the preferred embodiment of the invention, the radiation source is fitted with a notch filter to absorb infrared radiation having wavelengths to which the infrared detector is sensitive. In a further preferred embodiment, the apparatus detector is fitted with a band pass filter, which is complementary to the notch filter. In a further embodiment, there is included an apparatus for a scan means to raster-scan the infrared detector across the solder joint or across a circuit board having exposed solder joints. Preferably, the scan means generates a position signal corresponding to the position of each solder joint that the detector reads, i.e., measures the infrared emission. The position signed is preferably encoded on the signal from the infrared detector for identification and comparison purposes. In an alternative embodiment of the apparatus of the present system, the means to scan the infrared detector comprises a flying spot-scanner including optical means for focusing the infrared detector on the exposed solder joints and means to displace the optical axis of the optical means along a coordinate axis.

In a still further embodiment of the present invention, the apparatus has a means to generate an electronic analog signal from the infrared detector signal and from the scan means signal, said means to generate an electronic analog signal comprising an encoder, the signal output of said encoder being interfaced with said memory means.

DETAILED DESCRIPTION OF THE INVENTION

Figure 1:
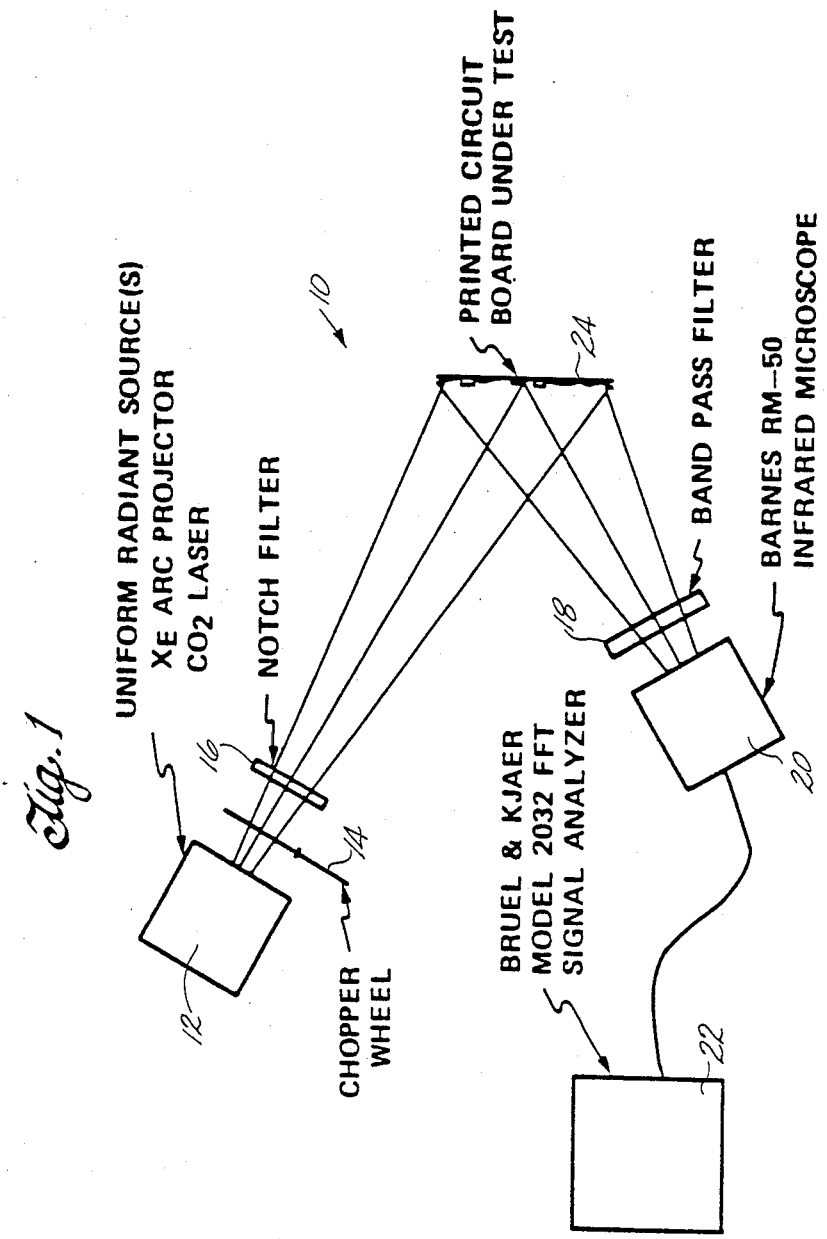
FIG. 1 is a schematic drawing of the solder joint analysis apparatus of the present invention.

Referring to FIG. 1, the solder joint analysis apparatus 10 comprises a radiant energy source 12, chopper wheel 14, notch filter 16, a band pass filter 18, an infrared detector 20, and a signal analyzer 22. The radiant energy source 12 can be an infrared source or a visible light source. Mercury-xenon arc projectors and $CO_2$ lasers have been employed, but other high-intensity radiant heat sources, such as halogen lamps, carbon arc lamps, and high-intensity tungsten lamps can also be utilized.

The chopper wheel is utilized to pulsate the radiation source. Preferably, the chopper wheel, which is motor-driven, is revolved at such a rate and has openings such that the radiant heat source is pulsed at a rate of less than 100 Hertz (Hz), preferably from about 1 Hz to about 10 Hz, most preferably at between about 2 Hz and 3 Hz. The notch filter is optional but preferred, and is designed to absorb infrared radiation from the radiant energy source to which the infrared detector is sensitive. The notch filter prevents such radiation from being reflected from the surface of circuit board 24 under test to the detector 20. A clear glass container containing water makes an excellent notch filter.

The band pass filter 18 is a conventional absorption filter, complementary to the notch filter, to further ensure that infrared radiation from the source does not reach the detector. The band pass filter is optional but preferred, since it limits the response of the infrared detector to a specific infrared radiation band for joint analysis.

The infrared detector 20 can be a conventional infrared detector, such as the Barnes RM-50 infrared microscope or the Hughes Aircraft THERMOSCAN TM System infrared detector. However, other infrared detectors can also be employed. The signal from the detector 20 is analyzed by a signal analyzer 22, such as a Bruel & Kjaer Model 2032 FFT signal analyzer. Other analyzers can be used including a cathode ray tube, imagers, printers, hard-print recorders, computer system analyzers, and the like.

The apparatus can be assembled from the Hughes Aircraft Company THERMOSCAN automatic printed circuit board and hybrid test system by adding a pulsed radiant energy source to the THERMOSCAN system. The signal-analyzing subsystem of the THERMOSCAN system can be modified with a signal processor and supporting software to obtain the information described herein. The THERMOSCAN system infrared detector scans the target in a pattern of 512 by 512 pixels (512 equidistant points for each of 512 equidistant lines).

The infrared detector continuously scans the board as the board is pulse illuminated. The detector scans the board in one (1) second or less. The THERMOSCAN system infrared detector scans the board in about 1/30 of a second. The board is tested, that is, pulse illuminated and scanned, for at least one (1) second, preferably for at least five (5) seconds, to obtain a number of readings and to increase the signal-to-noise ratio. Preferably, the pulse rate and the scan rate are not synchronized and have different durations so that the joints are scanned at different times during the heating cycle. For example, the board could be scanned every 33 milliseconds and the board could be illuminated at 2 Hz with a 50% duty cycle.

In the present system, all the solder joints on a circuit board are heated simultaneously. The entire board is radiated by a repetitive pulsed radiant energy source. (For very large boards, it may be necessary to irradiate and read subportions of the board sequentially.) The periodic course of the thermal image of the board is monitored with the infrared detector. The amplitude of the periodic temperature variation of a solder joint is determined by the electronic integrity of the joint as well as by the local environment of the joint, such as the number and conductivity of connecting circuit traces. By comparing the amplitudes of the T-oscillations of the solder joints on a board under test, with those T-oscillations of a substantially identical board having high electronic-integrity solder joints, the local environment effects are subtracted so that defective solder joints, such as solder joints with voids, unwetted solder joints, and the like can be identified. Solder joints with poor electronic integrity show different amplitude from solder joints with good electronic integrity at repetition periods comparable to the time it takes heat to diffuse between the joint and its connecting conductors. In an alternative embodiment, the phases of the temperature oscillation can be compared and, in addition, the fast Fourier transform of the temperature-time variation can be obtained and various moments of the transform compared, giving the system a greater sensitivity.

The theoretical considerations underlying the use of thermal imagery to analyze the electronic integrity of solder joints, is set forth in a paper presented at the Proceedings - 1986 IMIP Industry Review in Los Angeles, California, between Jan. 28th and 30th of 1986.

The whole board illumination or heating concept of the present system permits more efficient coupling of heat into the solder joints and improves signal analysis, because surface contamination of the board and joints is reduced. The analysis method of the present invention is more sensitive than other thermal sensing methods because of the whole-board heating concept. The apparatus used in the present system is simpler than other apparatuses for thermal analysis, because no focusing or mechanical motion of the radiant energy source or the circuit board is required. The detection of oscillating joint temperature excursions permits signal improvement due to increased number of the data samples taken. The scanning step of the present invention also permits monitoring the spacial variations of temperature across a single solder joint.

Infrared emission or absorption by a shiny solder surface is small compared to the conductive interchange of heat between the solder joint and its connecting conductive traces. Thus, the temperature variation will be sensitive to the interface contact quality between the solder joint and the copper traces. Heat conduction from the connecting conductive traces, which are heated by the radiant energy source along with the solder joint, to the solder joint can easily exceed the direct source radiation to the solder joint. In the heat balance for the copper traces, the heat load due to conduction of the underlying epoxy is comparable to the heat load due the copper's heat capacity. Infrared radiation from the copper traces is small compared to the heat conduction from the traces to the circuit board epoxy.

The radiant heat fluxes applied to the circuit board and the solder joints are less than about 100 watts per square centimeter, preferably less than about 10 watts per square centimeter, and most preferably about 5 watts per square centimeter. Pulsating radiant heating flux raises the average temperature of the solder joint by several tens of degrees (Celsius), with fluctuation amplitudes of several tenths of a degree. The infrared radiation emitted from the solder joints is read with a conventional IR detector, such as the detector on the THERMOSCAN automatic printed circuit board and hybrid test system. This detector has a TV scan rate and a temperature differential sensitivity of 0.1° C. or better. If a temperature rise of more than 10° C. is unacceptable because of the sensitivity of the components on the circuit board, a mask can be interdisposed between the circuit board and the radiant heat source. The mask will have holes at the location of the solder joints and connecting conductive traces, so that only the solder joints and the traces and their immediate vicinity are heated and the remainder of the circuit board is protected from additional heating. Such masks for the solder joints themselves are normally available because they are prepared for wave-soldering purposes.

The simplicity of the present system is a decided advantage over conventional thermal analyzers, which have a focus laser source and a detector which are mechanically moved from joint to joint. The present system eliminates the registration and programming requirements of the illuminating source for such systems. In addition, more information can be gathered on each joint in the present system when compared to the commercially available systems because repeated heating and reading cycles are performed on each joint. Since more information can be gathered, there is a corresponding improvement in the signal/noise ratio, which permits smaller temperature swings to be measured.

In an alternative embodiment of the invention, the board can be located in a curved infrared reflector, such as a chrome-faced parabolic disc which is larger than the board. The board is located so that illumination from the radiant energy source is reflected sideways from the reflector face onto the board to illuminate joints and conductive traces that are masked (fully or partially) at a perpendicular from the plane of the board by components on the board. The radiant energy source is positioned so that the board and the exposed portion of the curved reflector beyond the borders of the board are illuminated. The infrared emissions from such joints are reflected from the reflector to the infrared detector which scans the board and the exposed face of the reflector beyond the border of the board.

Figure 2:
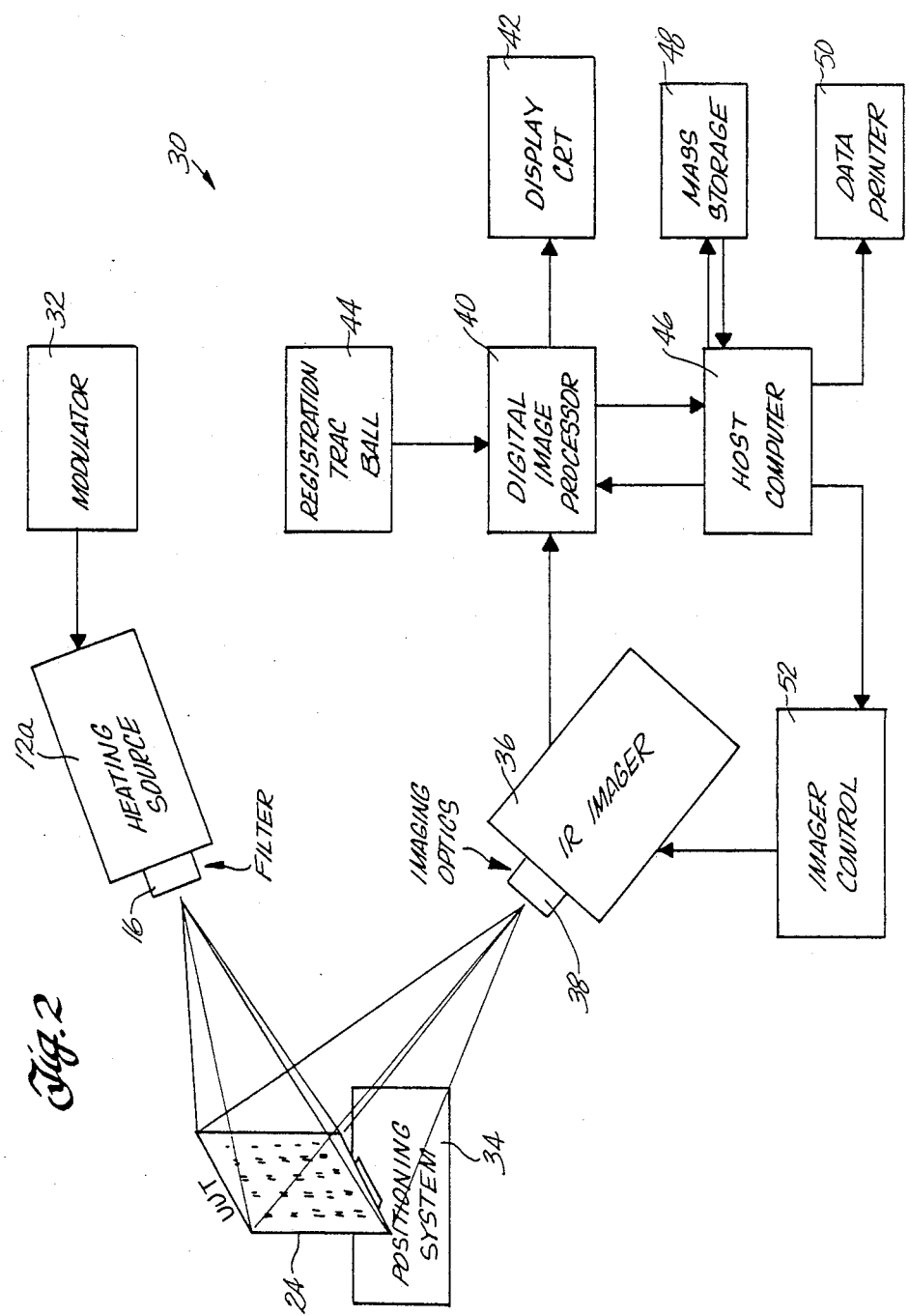
FIG. 2 is an alternative embodiment of the solder joint analysis apparatus of the present invention.

Referring to FIG. 2, an alternative embodiment of the present system is shown. System 30 comprises a modulator 32, a radiant heating source 12A, a notch filter 16, a circuit board positioning system 34 for supporting and carrying the circuit board 24, an IR imager 36 having imaging optics 38, a digital image processor 40, a display CRT (cathode ray tube) 42, a registration trac ball 44, a host computer 46, a mass storage 48, a data printer 50, and an imager control 52. Radiant heating source 12A illuminates circuit board 24 with a lighting source that is modulated by modulator 32. The heating source can be a strobe lamp or a lamp fitted with a chopper wheel. The heating source and the IR imager 36 are in fixed positions, and the positioning system 34, on which the circuit board is mounted, is aligned so that the IR imager can read the entire board or a large portion of the board, and the heating source can illuminate and heat the entire board or a large portion of the board. The IR imager, such as the IR imager on the THERMOSCAN test system, scans each joint on the board and records the temperature variation of each solder joint on the circuit board. The evaluation of each joint will depend on the differential temperature variation of the joint and the modulation frequency of the heating source.

The modulated heating source illuminates a large area at a modulation frequency of between about 1 Hz and about 10 Hz, preferably between about 2 Hz and about 3 Hz, so that the entire board or a large portion of the board is preferably uniformly illuminated. The energy density of the source is selected so that the heating source, during the analysis, will raise the temperature of the circuit board to a range of from about 70° to about 80° C. The heating source can be a strobe-type device or a device having a chopper wheel, as the device of FIG. 1. Filter 16 removes infrared radiation from the source illumination, to which the IR imager is sensitive, to prevent reflection of such radiation from the circuit board or surrounding fixtures to the IR imager.

The field of view of the IR imager can be as large as the source of illumination. Preferably, the image resolution of the IR imager is at least 1 mm so as to resolve each individual joint on the circuit board. With higher resolution, it is possible to obtain the spatial temperature distribution across each joint as well. The IR imager temperature resolution must be 1 part in 100 for a temperature between the range of about 50° to about 100° C. at a frequency response of at least 3 times the heating source modulation frequency. The image of each joint within the field of view must be addressable by the heating source and the IR imager. If the field of view of the IR imager is smaller than the board under analysis, the positioning system can be used to relocate the board, with respect to the IR imager and heating source, so that the IR imager will have an opportunity to scan the entire board by scanning different areas on the board sequentially.

The IR imager will preferably be sensitive to infrared radiation in the range of from about 3 to about 5 microns. IR frequency in that range has a higher specific detectivity. However, materials used in some boards, such as conformal coating, are opaque to 3-micron to 5-micron radiation. In such a case, an IR imager having a sensitivity in the 8 micron to 12 micron range can be used.

The process electronics must give a quantitative output of the differential amplitude of the joint. Since it has been found that the signal in the frequency domain gives the most information about the joint quality, synchronous detection at the source modulation frequency is desirable.

The signal from the IR imager 36 is received by the digital image processor 40, wherein the analog signal from the IR imager is converted to a machine-readable digital signal. A signal from the registration trac ball 44 is sent to the digital image processor 40 to encode the IR digital output signal for each joint so that the IR digital output signal can be identified with the particular solder joint. The IR reading of the circuit board can be displayed on the display CRT by transmitting the encoded signal to the display CRT. Of course, Fourier transform information does not need to be displayed on the CRT directly, but only some information indicative of defective joints, such as slope of the spectrum (frequency v. temperature), based on computer analysis of the Fourier spectrums. The encoded signal is transmitted to the host computer 46, which processes the signal into mass storage 48 and compares the signal with the IR output signal for a substantially identical circuit board having solder joints of known good electronic integrity. The host computer can transmit the encoded signal from the digital image processor 40 or the comparative results to the data printer 50. The computer can also transmit the comparative results to the digital image processor 40 for display on the display CRT. The host computer is pre-programmed with a conventional control program to control the imager controller, which in turn controls the imaging optics and/or the IR imager to have the IR imager scan the circuit board. Control programs such as the control program used in the scan control of the circuit board tester of U.S. Pat. No. 4,240,750, or the control program of the Hughes Aircraft THERMOSCAN system, can be modified for such usage.

Figure 3:
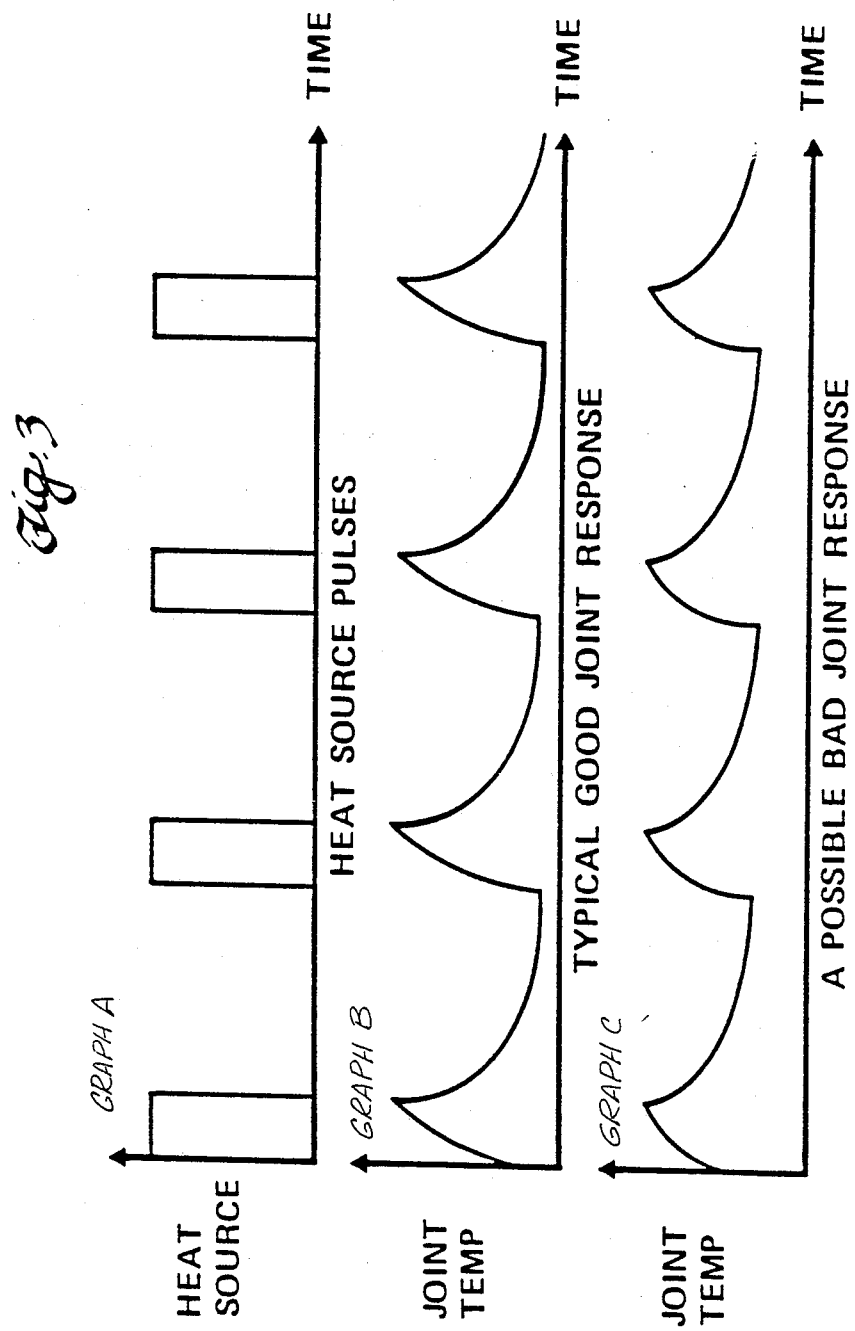
FIG. 3 comprises three graphs showing pulsed heating of a solder joint in accordance with the method of the present invention and temperature responses of a good solder joint and a bad solder joint.

Referring to FIG. 3, Graph A shows the heating pulses or cycles, with respect to time, of the radiant heat source on the printed circuit board. Graph B shows the typical IR response of a good solder joint on the circuit board. The temperature of the joints immediately commences to rise during each heating pulse and immediately commences to decay or cool at the end of each heating pulse. Graph C shows a possible bad joint response. The solder joint commences to heat up immediately during each heating cycle and commences cooling off at the completion of each heating cycle. However, the bad solder joint does not heat up to the same temperature as the corresponding good joint, nor does it cool off at the same rate as the corresponding good joint because of the poor conductive connection between the solder and the connecting copper traces and because of different solder mass. As mentioned above, the radiant energy source uniformly illuminates the surface of the circuit board thus furnishing energy to the traces as well as the solder joint. In a good solder joint, heat energy from the copper traces flows into the solder joint during the heating cycle and heat flows out of the solder joint into the copper traces during the cooling cycle.

Figure 4:
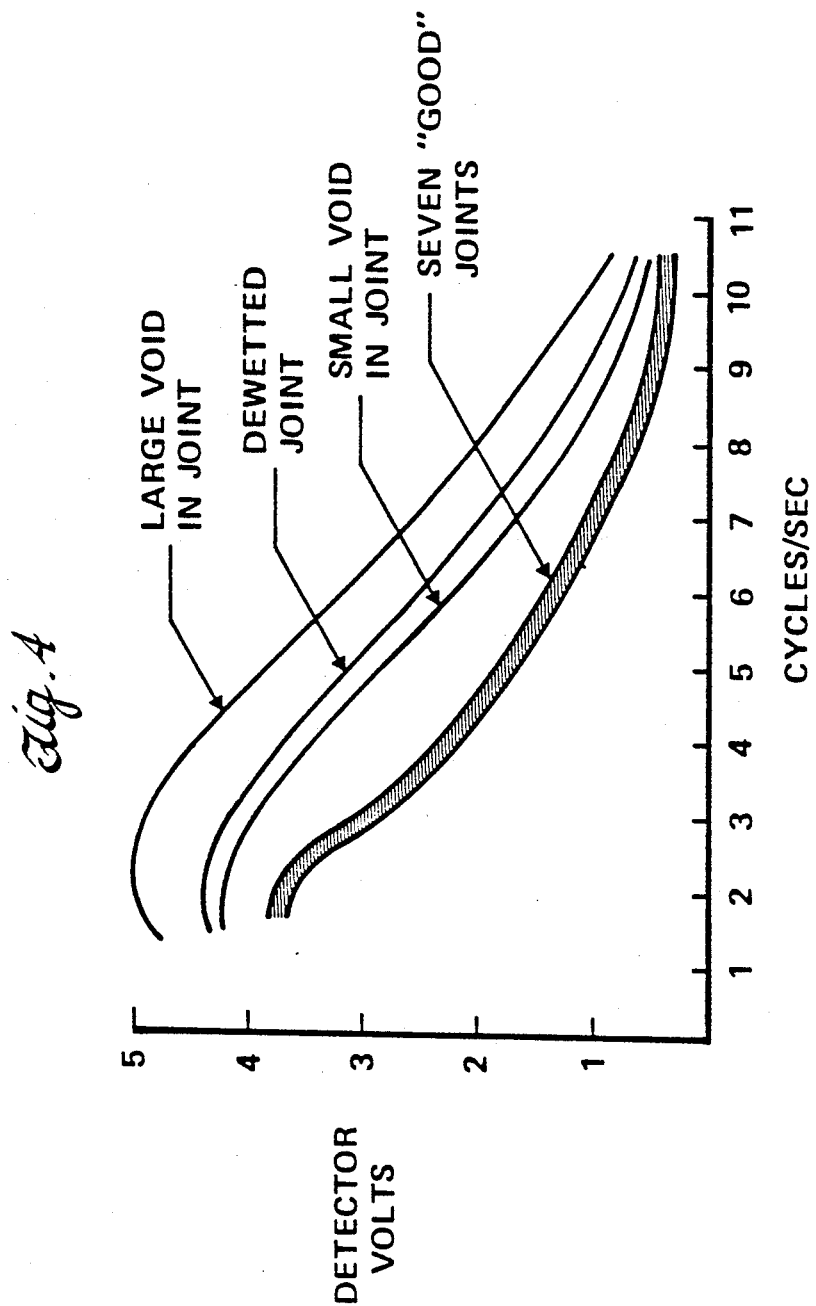
FIG. 4 shows the experimental Fourier spectrum of the infrared signature of good solder joints and defective solder joints for a pulse frequency of 3 Hz and a heating duty cycle of 10%.

FIG. 4 illustrates the IR response of a solder joint with regard to the heating frequency. Good joints and bad joints have their greatest response at less than 10 Hz, and for this particular experiment, between 2 Hz and 3 Hz. Bad joints give a fairly wide-variance response to heating, as is shown by the joint with the large void, the unwetted joint, and the joint with the small void. However, seven good joints, i.e., a specific good joint on seven different boards, give a fairly uniform IR response to heating. This illustrates that when a particular joint has an IR response variance of more than about 0.1 volt (about 0.2° C.) compared to a corresponding good joint, there is a high probability that the joint is a bad joint.

The following examples are included to further illustrate the practice of the present invention and are not intended to limit the scope of the invention.

EXAMPLE 1

An apparatus of the present invention was set up as illustrated in FIG. 1. The infrared detector 20 was a Barnes RM 50 infrared microscope, with its detector output directly coupled to a Bruel & Kjaer Model 2032 FFT signal analyzer. Solder joints on the circuit board were analyzed by sequentially registering each solder joint of the circuit board in the infrared microscope's field of view. The scanning optics of the infrared microscope were stopped, causing the microscope to register at a single point on the solder joint.

The emissivity of organic material is much higher than solder in the 1.8-micron to 5-micron spectral range to which the infrared microscope is sensitive. Accordingly, surface contamination on the joints strongly influences the magnitude of the detector signal. By using a signal analyzer to measure frequency response, the effect of the surface contamination upon the infrared measurement was minimized. Surface contamination is reported to be a troublesome source of noise for conventional laser/inspect systems. Surface contamination in small amounts alters the infrared emissivity, while large amounts of surface contamination can mask or conceal the surface of the solder from the heating radiation and the infrared emissivity. One of the advantages of the whole board illumination approach of the present invention is that most of the radiant energy of the source is absorbed by the much higher emissivity substrate material of the board and then conducted via the traces to the joints. Surface contamination of the board causes a much smaller proportionate change in the emissivity of the board.

Two illumination sources were tried. The first radiant heat source 12 was a carbon dioxide laser delivering about 4 watts peak power to a spot about 3 mm across, which is approximately the size of a single solder joint, to give an energy flux of about 56 watts/sq. cm. The second radiant heat source 12 was a mercury-xenon lamp of 800 watts peak power, which could deliver about 10 watts per square centimeter over 30 square centimeters. A water cell was employed as a notch filter to absorb the 1.8-micron to 5-micron infrared output of the mercury-xenon lamp. The carbon dioxide laser provided the largest signal with the least heating of the board and components because of the energy flux. The mercury-xenon arc lamp produced barely detectable temperature swings, because of the low energy flux, and heated the board considerably. It has been found that for a given energy density or flux, laser and arc lamp illumination sources give substantially similar results. The use of a lock-in amplifier tuned to a (swept) sinusoidal modulation frequency was subsequently found in a series of experiments to improve the signal-to-noise ratio enough to make area illumination satisfactory.

The illumination from the laser and the arc lamp was modulated in a square-wave fashion using a mechanical chopper. The illumination was pulsed at about 2.63 Hz with an illumination period of 30 milliseconds, that is, the illumination was switched on for about 30 milliseconds and was switched off for about 350 milliseconds.

The circuit boards used in the test were of commercial construction with through-plated holes and full-solder masking. Single components were hand-soldered in place on the boards to provide a controlled population of defective solder joints. Ten identical boards were prepared and each board had a single solder joint. Seven boards had good solder joints, two boards had solder joints containing voids, and the last board had a solder joint that was soldered without flux to give a totally unwetted solder joint.

The best results were obtained using the carbon dioxide laser to heat the joints while the signal analyzer operated as a synchronous averager (boxcar integrator) to minimize the electrical detector noise. Ten samples, of 16 seconds each, provided ample frequency discrimination and signal-to-noise ratio.

The fast Fourier transform capabilities of the signal analyzer were used to emphasize the differences in temperature vs. time curves. Curves which could not be readily distinguished by eye in the time domain could be easily distinguished with Fourier transforms. The results are shown in FIG. 4 as a frequency response plot. The vertical axis is the detector output in volts, which is monotonically related to the solder joint temperature. For the small temperature variations, the detector output may be considered approximately proportional to the first power of the temperature. The horizontal axis is the frequency in cycles per second. FIG. 4 is the Fourier transform of the joint temperature vs. time curve.

The joints containing voids have less heat capacity, so they heat up and cool down faster than do the good joints. In the unwetted joint, the solder did not fill the barrel of the hole in the circuit board, resulting in low joint mass, which accounted for the rapid temperature changes.

EXAMPLE 2

Figure 5:
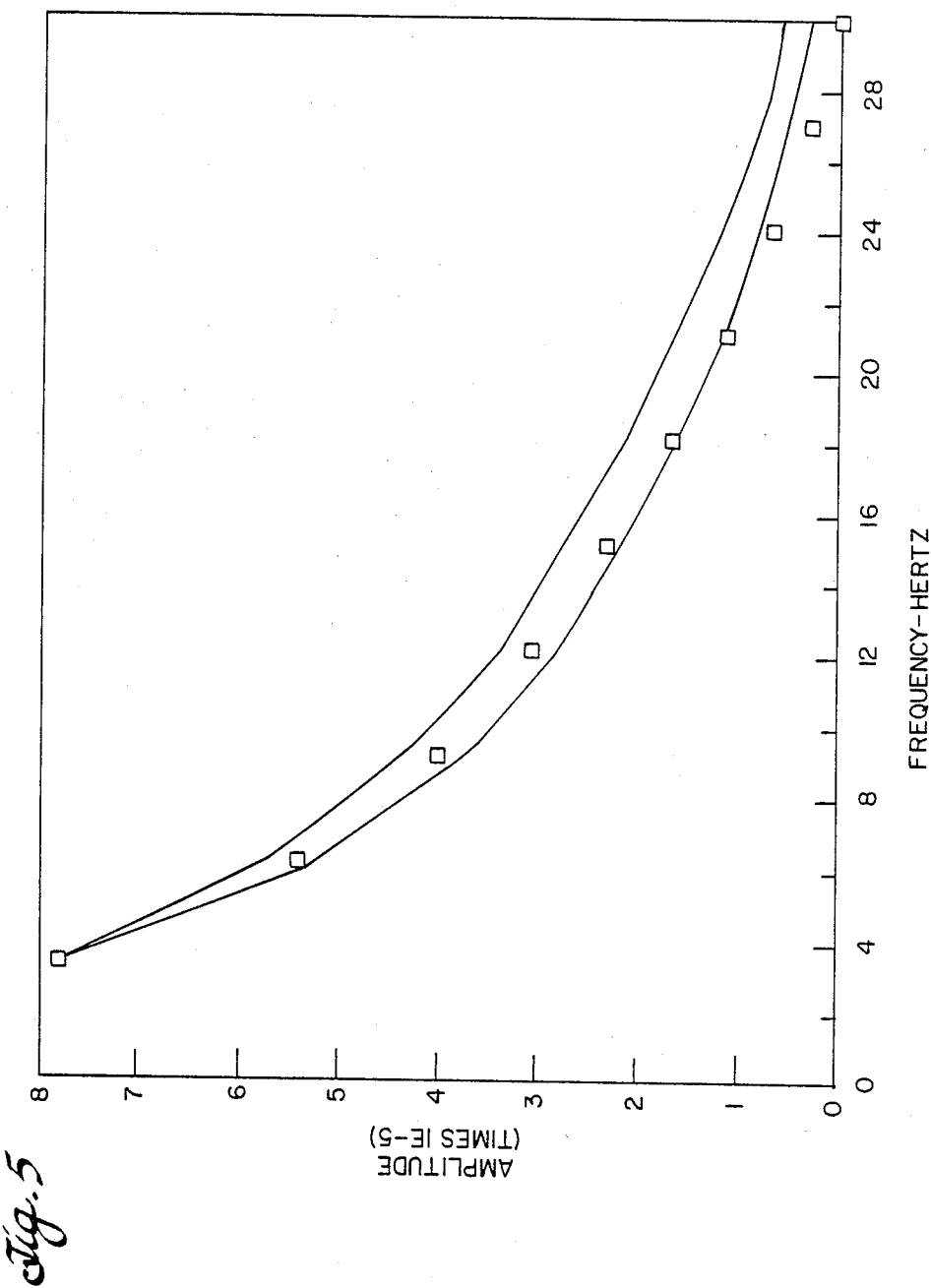
FIG. 5 is the theoretical predicted Fourier transform of the joint temperature for the heating pulse sequence which gave the experimental results of FIG. 4. The response squares indicate the theoretical predictions, and the curves denote the experimental range of values for the good joints.

During the heating cycle, the ratio of the solder surface temperature ($T_{s1}$) and the ambient temperature ($T_o$) can be represented by the following formula:

$$T_{s1}/T_o = (S_1/8\sigma T_o^4) \left[ \left( \frac{\epsilon_{Cu}}{\epsilon_s} \right) \frac{K_s(k_- - k_+)}{a\rho_{Cu}C_{Cu}i\omega + K_s\beta_E + \epsilon_{Cu}\sigma 4T_o^3} + e^{-k_+l} - e^{-k_-l} \right] \Delta^{-1} \text{ whereas}$$

$$\Delta = e^{-k_+l}\left(1 + \frac{K_s k_-}{4\epsilon_s\sigma T_o^3}\right) - e^{-k_-l}\left(1 + \frac{K_s k_+}{4\epsilon_s\sigma T_o^3}\right)$$

$$k_\pm = -\frac{\alpha}{2} \pm \frac{1}{2}[\alpha^2 + 4\beta_s^2]^{\frac{1}{2}}$$

$$\beta_s^2 = i\omega\rho_s C_s/K_s$$

$$\beta_E^2 = i\omega\rho_E C_E/K_E$$

wherein
$K_s = 4.62 \times 10^6$ erg/sec cm° K.
$K_E = 1.4 \times 10^4$ erg/sec cm° K.
$P_{cu} = 8.91$ g/cc
$C_{cu} = 0.384 \times 10^7$ erg/cm° K.
$\theta = 0.567 \times 10^{-4}$ erg/sec cm$^2$° K.$^4$
$a = 2.5 \times 10^{-2}$ cm
$l = 0.1$ cm $T_o = 300°$ K.
$\epsilon_{cu} = 0.2$
$\epsilon_s = 0.2$
$\omega = (1-10^2) \sec^{-1}$
$S_1 = 1-5$ watts/cm$^2$
$i = -1$ To confirm reliability of the equation, an experiment was carried out using the apparatus of FIG. 1 employing a step-function source with a 10% duty or heating cycle at about 3 Hz. To compare the model of the above equation with the experiment, the 10% duty cycle, 3 Hz pulse train was Fourier-analyzed to find the frequency components for harmonics up to 60 Hz, and folded in with the foregoing equations. The experimental data for the good solder joints was scaled to the calculation by tying the data to the Fourier calculation at 3 Hz. Comparative results are shown in FIG. 5. The experimental data has the same general shape as the calculation, but does not fall quite as steeply. Considering the simplified model used for the calculation, the agreement between the model equation above and the experiment is remarkable.

EXAMPLE 3

There were traces of nonwetting at the edges of the solder fillets of some of the good joints of the circuit boards used in the experiment of Example 1. In addition, in some of the circuit boards with good joints, there was an imperfect fill of the solder through the plated hole. To determine if the variation in appearance of solder joints due to hand-soldering were masking the effects of the imperfections noted, the temperature vs. time curves for a group of consumer-grade circuit boards were measured. Consumer-grade circuit boards were machine-soldered employing dip, drag, or wave-soldering techniques. These circuit boards were not of the plated through-hole variety. Visually, the size and the shape of the solder fillets in the boards was highly uniform. There was a slight mottling in the surface finish, but, in general, the board looked better than the hand-soldered boards. Out of a population of 18 consumer-grade circuit boards, 5 were measured. The scatter was comparable to that of the hand-soldered boards and comparable to that reported by J. Maki of the China Lake Naval Weapons Center, for solder joints inspected with a Vanzetti solder inspection machine.

EXAMPLE 4

The apparatus of Example 1 was modified by replacing the spectrum analyzer with a lock-in amplifier. The radiant heat source was a carbon dioxide laser. The 10.6-micron radiation was chapped and used to illuminate a section of the PC board surrounding the joint to be measured. A Barnes IR microscope was used to image the joint and measure the temperature swing of the joint during the heating and cooling phases. The IR microscope measured radiation in the 3-micron to 5-micron range spectrum and did not see the 10.6-micron radiation used to illuminate the joint. The IR microscope displays a visual image of the infrared radiation emitted from the board on a cathode ray tube. The luminance of the CRT image is proportional to the effective radiance of the viewed object and can be related to the temperature of the object. Any single scan line of the CRT is available for viewing as a function of luminance. In particular, the scan line can be positioned on the center of a joint, and the temperature profile across the board and through the joint can be viewed as a function of luminance.

An automated X-Y stage was used to position the board so that a representative selection of joints could be viewed each time by a selection of the proper scan line. The X-Y stage was necessary, because the boards to be tested were larger than the field of view of the infrared microscope. The stage controller was programmed to locate the same series of joints in a selected order for each test.

The measurements were made using a EG&G Model 5301 lock-in amplifier to read the differential temperature signal from the infrared microscope. The lock-in amplifier searches the frequency spectrum of the signal, then "locks in" the frequency with the largest amplitude signal, or designated frequency, and only measures the amplitude of signals with the same frequency and phased as the designated signal. To find the differential temperature variation of a selected joint, the joint was placed in the center of the field of view of the infrared microscope. The microscope was then zoomed-in on the selected joint until it filled the entire field of view. The scan line through the center of the joint was displayed. This gave a signal proportional to the temperature at the very center of the joint. This signal could be seen to vary in temperature at the chopping frequency. This signal was then fed to the lock-in amplifier for analysis. Once the signal could be locked in, only the signal component, at the chopping frequency, would give significant results. The differential amplitude for defective joints was consistently larger than the differential amplitude for good joints. These results show that measurements made in the frequency domain can be made to be more sensitive than measurements made in the time domain. The optimum frequency of operation is that corresponding to the time that it takes heat to flow in and out of the joint.

EXAMPLE 5

Employing the apparatus of Example 1, the infrared emissivity of solder joints on a circuit board were conducted with a carbon dioxide laser spaced at various distances from the board to vary the heat energy on the board. At a spacing of 1 foot, only the solder joint under test was radiated. At 3 feet, and area containing 3 to 4 joints was radiated. The radiant energy at 5 feet from the carbon dioxide laser was insufficient to cause notable heating of the joints. It was found that the peak differential temperature occurred when the laser was spaced 3 feet from the board. This supports the theoretically predicted advantage of whole board illumination over single joint illumination.

The experiment was repeated by positioning the laser 3 feet from the circuit board and the infrared emissivity of the joints were examined at chopping frequencies of 2.5 Hz, 3.0 Hz, 4.0 Hz, 5.0 Hz, and 10 Hz. The peak differential temperature occurred at a chopping frequency of from 3 Hz to 5 Hz. Optimum pulse frequency is the inverse of the time it takes heat to flow in and out of a joint. This depends on joint mass and the number of conducting traces attached to the joint. In subsequent experiments the optimum frequency was found to be from about 2 Hz to about 3 Hz.

EXAMPLE 6

The apparatus of Example 4 was modified by replacing the carbon dioxide laser with a mercury-xenon arc lamp as the thermal radiation source. The arc lamp radiated and illuminated the whole board. This is the preferred method of heating, since it is less sensitive to changes in solder joint emissivity due to contaminants. For a given power density, whole board illumination increases the differential temperature variation of a joint and gives a better signal-to-noise ratio because more heat is supplied to the joint by conduction from the traces than from direct radiation. Ten identical printed circuit boards were obtained. The boards were approximately 3"×5", with 52 solder joints on one side. The copper traces connected many of the joints to other joints.

Figure 6:
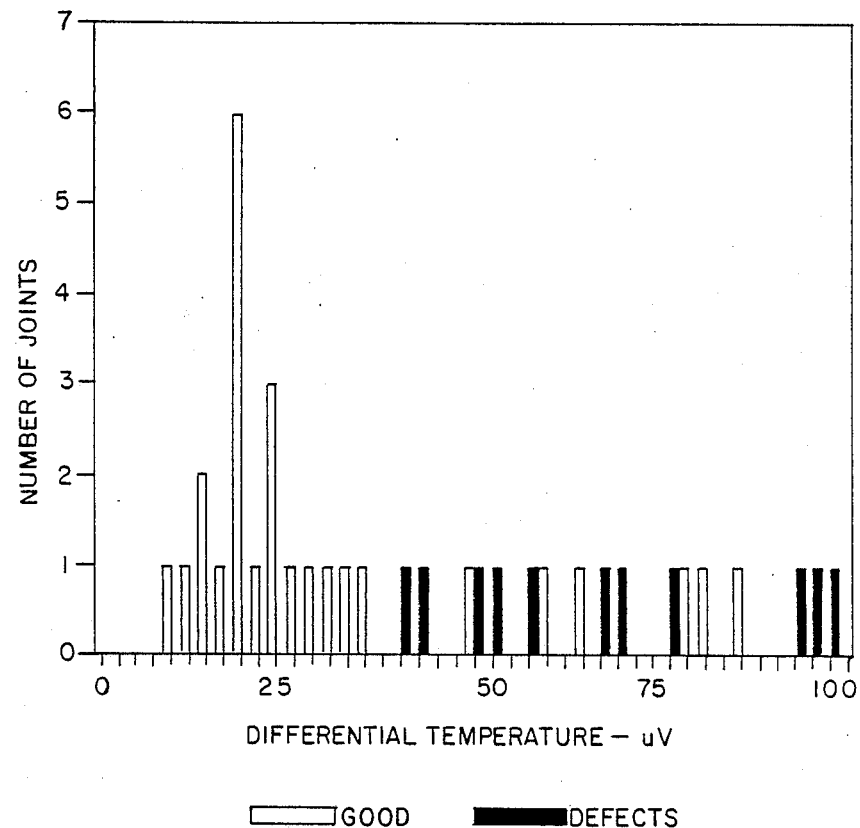
FIG. 6 is a bar graph showing the experimentally determined temperature differential as microvolts for good solder joints and defective solder joints, for a pulse repetition rate of 3 Hz and a heating duty cycle of 50%.

The Barnes infrared microscope was zoomed-in on a joint, the chopper frequency was set, and the lock-in amplifier was set and allowed to stabilize for each joint. The temperature differential for each joint was measured. Again, it was found that the differential temperature was significantly higher for defective joints than for good joints as shown in FIG. 6. The majority of good joints had a measured differential temperature of less than 37 microvolts, whereas all the defective joints had a measured temperature differential in excess of 37 microvolts. This experiment showed that whole board illumination for heating is superior to single-source-point heating of a solder joint.

EXAMPLE 7

The apparatus of Example 6 was employed for this experiment. Fifty printed circuit boards were obtained, each board having 6 solder joints. The boards did not have copper traces. Results from this experiment were less predictable than the results of circuit boards tested in Example 6. The spread differential temperature of the boards in this Example, increased from 3-to-1 to 10-to-1 in some instances. Because of the widespread measurement of the temperature differentials of some of these boards without copper traces, it was difficult to find a meaningful correlation between the measurements and the results of visual inspection. It is believed that this is due, in large part, to the fact that these boards did not have copper traces. We believe that copper traces are important for the advantage of whole board illumination to be realized, since, according to our calculations, most of the heat going into a solder joint comes from conduction via the copper traces.

Of the 6 solder joints on each board, 4 showed that visually bad joints did have a higher differential temperature than the good joints. Joints with excessive solder defects also showed a higher differential temperature on 3 of the 6 joints of each board. Some of the solder joints showed quite high temperature differentials, and it is suspected that these joints have hidden voids. The results from Examples 6 and 7 suggest that exposed connecting copper traces or near-subsurface traces within a trace width of the surface must be present along with solder joints on printed circuit boards tested by whole board illumination. The advantage of whole board illumination, that is, illumination of the joint and connecting exposed or near-subsurface conductive traces, is based on the principle that heat flows in and out of the joint through the traces.

What is claimed is:

1. An apparatus for inspecting the electronic integrity of an exposed solder joint connected to conductive traces comprising:
    (a) a radiation source for flood-heating the exposed solder joint and connecting conductive traces and surrounding board to heat the exposed solder joint and the exposed connecting traces;
    (b) an infrared detector for detecting the infrared radiation emitted from said exposed solder joint and for generating a signal corresponding to the intensity of the detected infrared radiation;
    (c) conversion means to convert the signals from the infrared detector into machine-readable inspection information;
    (d) memory means for storing the machine-readable inspection information and the machine-readable standard information depicting an infrared profile of a substantially identical solder joint connected to conductive traces of good electronic integrity; and
    (e) means to compare the machine-readable inspection information against the machine-readable standard information to quantify differences in the infrared profile of the solder joint under test and a similar solder joint of good electronic integrity.

2. The apparatus according to claim 1 wherein the radiation source includes a notch filter for absorbing infrared radiation of a selected wavelength from the radiation source.

3. The apparatus according to claim 1 wherein the infrared detector includes a cutoff filter for absorbing radiant energy of a preselected wavelength.

4. The apparatus according to claim 1 wherein the apparatus includes means to raster-scan the solder joint with the infrared detector.

5. The apparatus according to claim 4 wherein the means to raster-scan the solder joint with the infrared detector also generates a position signal corresponding to each signal generated by said infrared detector, said conversion means converting the position signal to machine-readable position information and encoding said information with said machine-readable inspection information.

6. The apparatus according to claim 4 wherein said means to raster-scan the solder joint with the infrared detector comprises a flying spot-scanner, said flying spot-scanner including optical means for focusing said infrared detector on said joint, said optical means including means to displace the optical axis of said optical means along a coordinate axis.

7. The apparatus according to claim 1 wherein the radiation source includes means to modulate the radiation.

8. The apparatus according to claim 1 wherein the radiation source is a visible light source.

9. The apparatus according to claim 1 wherein the radiation source is an infrared source.

10. The apparatus according to claim 1 wherein the radiation source is a mercury-xenon lamp.

11. The apparatus according to claim 1 wherein the radiation source is a carbon dioxide laser.

12. An apparatus for inspecting the electronic integrity of exposed solder joints connected to conductive traces on a circuit board comprising:
    (a) a pulsed radiation source for flood-heating a circuit board having exposed solder joints and connecting conductive traces to heat the exposed solder joints and connecting traces;
    (b) an infrared detector for detecting the infrared radiation emitted from said exposed solder joints and for generating a signal corresponding to the intensity of the detected infrared radiation;
    (c) means to raster-scan the solder joints with the infrared detector;

(d) conversion means to convert signals from the infrared detector into machine-readable inspection information;

(e) memory means for storing the machine-readable inspection information and machine-readable standard information depicting an infrared profile of a substantially identical circuit board having solder joints of good electronic integrity; and (f) means to compare the machine-readable inspection information against the machine-readable standard information to quantify differences in the infrared profile of the solder joints under test and solder joints of good electronic integrity.

13. The apparatus according to claim 12 wherein the radiation source includes a notch filter for absorbing infrared radiation of a selected wavelength from the radiation source.

14. The apparatus according to claim 12 wherein the infrared detector includes a cutoff filter for absorbing radiant energy of a preselected wavelength.

15. The apparatus according to claim 12 wherein the means to raster-scan the solder joints with the infrared detector also generates a position signal corresponding to each signal generated by said infrared detector, said conversion means converting the position signal to machine-readable position information and encoding said information with said machine-readable inspection information.

16. The apparatus according to claim 12 wherein said means to raster-scan the solder joints with the infrared detector comprises a flying spot-scanner, said flying spot-scanner including optical means for focusing said infrared detector on said joints, said optical means including means to displace the optical axis of said optical means along a coordinate axis.

17. The apparatus according to claim 12 wherein the radiation source includes means to modulate the radiation to get repetitive pulses.

18. The apparatus according to claim 12 wherein the radiation source is a visible light source.

19. The apparatus according to claim 12 wherein the radiation source is an infrared source.

20. The apparatus according to claim 12 wherein the radiation source is a mercury-xenon lamp.

21. The apparatus according to claim 12 wherein the radiation source is a carbon dioxide laser.

22. The apparatus according to claim 17 wherein the modulation means is a chopper wheel.

23. The apparatus according to claim 12 wherein the radiation source flood-heats the entire surface of the side of the circuit board having exposed solder joints.

24. A method for inspecting the electronic integrity of solder joints on a circuit board comprising:

(a) applying pulsed radiant energy to the side of the circuit board having exposed solder joints and connecting conductive traces to heat said exposed solder joints and connecting conductive traces;

(b) detecting the infrared radiation emitted from the solder joints; and (c) comparing under similar conditions the infrared radiation profile of the solder joints undergoing inspection against the infrared radiation profile of similar solder joints of known good electronic integrity to quantify differences in the infrared profiles to determine if the solder joints under test have good or bad electronic integrity.

25. A method for qualitatively inspecting the electronic integrity of a solder joint comprising:

(a) applying modulated radiant energy to a solder joint to heat the solder joint and any connecting conductive traces;

(b) measuring the infrared radiation emitted from the solder joint under test with an infrared detector which converts the infrared radiation into electrical signals;

(c) observing the signal response of the infrared detector; and (d) comparing the signal response of the infrared detector of the solder joint under test with previously determined signal responses characteristic of either unacceptable or acceptable solder joints so as to determine the acceptability of the solder joint.

26. The method according to claim 25 wherein the modulated radiant energy is pulsed to the solder joint at a frequency between about 1 Hz and about 10 Hz.

27. The method according to claim 25 wherein the modulated radiant energy is applied to the solder joint for between about 50 milliseconds and about 500 milliseconds per pulse.

28. The method according to claim 27 wherein the time between each pulse is between about 50 milliseconds and about 950 milliseconds.

29. The method according to claim 25 wherein each pulse of radiant energy has a duration of between about 160 milliseconds and about 250 milliseconds and the duration between pulses is between about 160 milliseconds and about 250 milliseconds.

30. A method for determining the electronic integrity of solder joints on a circuit board comprising:

(a) pulse-heating the side of the circuit board with exposed solder joints and exposed connecting conductors to heat the solder joints;

(b) measuring the temperature changes of each exposed solder joint during the pulsed heating and non-heating to produce a thermal signal proportional to the amplitude of the temperature differential of each solder joint;

(c) sampling each said thermal signal and digitally storing a value corresponding to the sampled thermal signal produced for a similar solder joint of good electronic integrity; and (d) thereafter comparing said thermal signal with a signal proportional to the stored digital value to quantify the thermal response of the tested solder joint to the similar solder joint of good electronic integrity.

31. The method according to claim 30 wherein the heating and measuring steps are sequentially repeated to obtain a stable infrared profile for each heating phase.

32. A method for inspecting the electronic integrity of exposed solder joints on a circuit board comprising:

(a) applying a pulsed radiant energy to the side of a circuit board having exposed solder joints with connecting conductive traces to heat the solder joints and the connecting conductive traces;

(b) reading the infrared response of the solder joints employing an infrared transducer to generate an electrical signal proportional to the infrared response of each solder joint;

(c) processing the electrical signal to determine the temperature differential of each solder joint in response to the pulsed heating; and (d) comparing the temperature differential of the joints under test with previously determined temperature differentials of similar solder joints of acceptable or unacceptable electronic integrity so as to determine the acceptability of the solder joints.

33. The method according to claim 32 wherein the circuit board is heated with a pulsed radiant energy source and the infrared response of the solder joints is continuously read to determine the temperature oscillation of each joint during the heating and non-heating periods.

34. The method according to claim 33 wherein the temperature oscillation of each solder joint is compared against predetermined temperature oscillation to determine if the solder joint under test has a temperature oscillation profile of a defective solder joint or the temperature oscillation profile of a solder joint of good electronic integrity.

35. The method according to claim 33 wherein the Fourier spectrum of the temperature oscillation of each solder joint is compared against the predetermined Fourier spectrum of a temperature oscillation to determine if the solder joint under test has a temperature oscillation profile of a defective solder joint or the temperature oscillation profile of a solder joint of good electronic integrity.

36. A method for inspecting the electronic integrity of solder joints on a circuit board comprising:
  (a) applying pulsed radiant energy to the side of the circuit board opposite the side having exposed solder joints and connecting conductive traces to heat said exposed solder joints and connecting conductive traces;
  (b) detecting the infrared radiation emitted from the solder joints; and
  (c) comparing under similar conditions the infrared radiation profile of the solder joints undergoing inspection against the infrared radiation profile of similar solder joints of known good electronic integrity to quantify differences in the infrared profiles to determine if the solder joints under test have good or bad electronic integrity.

* * * * *